(12) United States Patent
Hatanaka et al.

(10) Patent No.: US 7,944,203 B2
(45) Date of Patent: May 17, 2011

(54) CORROSION EVALUATION DEVICE AND CORROSION EVALUATION METHOD

(75) Inventors: Hiroaki Hatanaka, Yokohama (JP); Katsuya Toda, Tokyo (JP); Minoru Tagami, Yokosuka (JP)

(73) Assignee: IHI Corporation (JP)

( * ) Notice: Subject to any disclaimer, the term of this patent is extended or adjusted under 35 U.S.C. 154(b) by 400 days.

(21) Appl. No.: 12/097,846

(22) PCT Filed: Dec. 18, 2006

(86) PCT No.: PCT/JP2006/325172
§ 371 (c)(1),
(2), (4) Date: Jun. 17, 2008

(87) PCT Pub. No.: WO2007/072774
PCT Pub. Date: Jun. 28, 2007

(65) Prior Publication Data
US 2009/0134867 A1    May 28, 2009

(30) Foreign Application Priority Data

Dec. 19, 2005 (JP) .................................. 2005-364387
Nov. 15, 2006 (JP) .................................. 2006-309165

(51) Int. Cl.
*G01R 33/02* (2006.01)
(52) U.S. Cl. .................................. 324/252; 324/207.21
(58) Field of Classification Search ............. 324/207.21, 324/228–229, 249, 252
See application file for complete search history.

(56) References Cited

U.S. PATENT DOCUMENTS 6,504,363 B1 * 1/2003 Dogaru et al. ................. 324/235
7,107,154 B2 * 9/2006 Ward .............................. 702/6
7,487,846 B2 * 2/2009 Head et al. ..................... 175/61
2002/0158626 A1 * 10/2002 Shay et al. ............... 324/207.16
2005/0280411 A1 * 12/2005 Bicking .................. 324/207.21

FOREIGN PATENT DOCUMENTS

| JP | 5-172786 A | 7/1993 |
| JP | 6-294850 A | 10/1994 |
| JP | 2003-179283 | 6/2003 |

(Continued)

OTHER PUBLICATIONS

International Search Report dated Mar. 13, 2007, in corresponding PCT Application No. PCT/JP2006/325172.

(Continued)

*Primary Examiner* — Bot L LeDynh
(74) *Attorney, Agent, or Firm* — Ostrolenk Faber LLP (57) ABSTRACT

A corrosion evaluation device for performing a quantitative evaluation of corrosion by measuring a quantity of decrease in the thickness of a magnetic material which is covered by a non magnetic material or a magnetic material which is not covered by a non magnetic material which includes: a magnetic field generating device for generating such a magnetic field that includes the magnetic material in a magnetic path, a Giant Magnet-Resistive effect (GMR) sensor provided with a GMR sensor for detecting a magnetic flux leakage with regard to the magnetic material and converts a change in the magnetic flux into an electrical signal, a thickness reduction calculation portion for calculating a quantity of decrease in the thickness of the magnetic material based on the electrical signal. The corrosion evaluation device precisely performs a quantitative evaluation of corrosion even when the magnetic material, which is to be evaluated, is covered by a non magnetic material.

9 Claims, 7 Drawing Sheets

FOREIGN PATENT DOCUMENTS

JP          2005-3405 A        1/2005

OTHER PUBLICATIONS

Yasuhiro Kataoka et al., "GMR Licenser o Mochiita Roei Jisokuho ni yoru Kekkan Kenshutsu", The Institute of Electrical Engineers of Japan Magnetics Kenkyukai Shiryo, MAG-00-237~252, Nov. 8, 2000, pp. 73 to 78.

Yasuhiro Kataoka et al., "Mu Shikosei GMR Sohi to Roei Jisoku Shinshoho eno Oyo no Teian", The Institute of Electrical Engineers of Japan Magnetics Kenkyukai Shiryo, MAG-01-190~199, Dec. 3, 2001, pp. 37 to 40.

* cited by examiner

CORROSION EVALUATION DEVICE AND CORROSION EVALUATION METHOD

CROSS REFERENCE TO RELATED APPLICATIONS

The present application is a 35 U.S.C. §371 National Phase conversion of PCT/JP2006/325172, filed Dec. 18, 2006, which claims priority of Japanese Application No. 2005-364387, filed Dec. 19, 2005, and Japanese Application No. 2006-309165, filed Nov. 15, 2006, the disclosures of which have been incorporated herein by reference. The PCT International Application was published in the Japanese language.

TECHNICAL FIELD

The present invention relates to a corrosion evaluation device and a corrosion evaluation method.

BACKGROUND ART

A Magnetic Flux Leakage Method (MFL), which measures quantity of decrease in the thickness of the steel material by adding a magnetic field to the steel material and detecting a change of magnetic flux leakage, has been conventionally used as one of the methods to quantitatively evaluate the progress of corrosion in steel material (magnetic material) which are used for pipelines of oil or gas, a bottom plate of a crude oil tank, and the like. In such a Magnetic Flux Leakage Method, a hall element is generally used as a sensor for detecting magnetic flux leakage.

For example, in Japanese Unexamined Patent Application, First Publication No. 2005-3405, a technology to detect a ruptured portion of reinforcing steel covered by concrete, which is a non magnetic material, is disclosed. This technology detects a remaining magnetism of the reinforcing steel with a magnetic sensor and detects a portion where a large amount of magnetic flux leakage is generated as a ruptured portion.

DISCLOSURE OF INVENTION

Problem to be Solved by the Invention

Now, in the magnetic flux leakage method that used a hall element as a magnetic sensor, because magnetic sensitivity of the hall element is weak, when the steel material, which is an object to be evaluated, is covered by a non magnetic material such as concrete or the like, it was not possible to precisely detect the magnetic flux leakage and so it was difficult to perform quantitative evaluation of corrosion. That is, a ruptured portion of the steel material covered by a non magnetic material such as concrete or the like can be detected, but it is not possible to perform quantitative evaluation of corrosion.

Furthermore, for a method to detect corrosion of steel material covered by a non magnetic material, an electrochemical measurement method such as a self-potential method, polarization resistance method, or the like is given. However, these methods can determine the presence of corrosion, but quantitative evaluation cannot be performed.

The present invention was made in view of the above-described circumstances. An object of the invention is, that even if a magnetic material which is an object to be evaluated is covered by a non magnetic material, a precise quantitative evaluation can be performed.

Means for Solving the Problem

In order to achieve the above-described object, as a first solution for solving the problem, a device is employed which is a corrosion evaluation device for performing a quantitative evaluation of corrosion by measuring a quantity of decrease in the thickness of a magnetic material which is covered or not covered by a non magnetic material including: a magnetic field generating device for generating such a magnetic field that includes the magnetic material in a magnetic path, a GMR sensor, which includes a GMR element for detecting a magnetic flux leakage with regard to the magnetic material, for converting the change in the magnetic flux to an electrical signal, a thickness reduction calculation device for calculating the quantity of decrease in the thickness of the magnetic material based on the electrical signal.

A second solution for solving the problem is the corrosion evaluation device in accordance with the first solution for solving the problem in which the GMR sensor is formed by a bridge circuit using the GMR element.

A third solution for solving the problem is the corrosion evaluation device in accordance with the first or the second solution for solving the problem in which the quantity of decrease in the thickness is measured at each of a predetermined measuring points while two-dimensionally moving along the magnetic material.

A fourth solution for solving the problem is the corrosion evaluation device in accordance with the third solution for solving the problem in which a distance between the surface of the magnetic material and the GMR sensor is maintained constant and moved.

A fifth solution for solving the problem is the corrosion evaluation device in accordance with any one of the first to the fourth solution for solving the problem in which the magnetic material is a reinforcing steel or a steel plate.

A sixth solution for solving the problem is the corrosion evaluation device in accordance with any one of the first to the fifth solution for solving the problem in which the non magnetic material is concrete.

As a seventh solution for solving the problem, a method is employed which is a corrosion evaluation method for performing a quantitative evaluation of corrosion by measuring a quantity of decrease in the thickness of a magnetic material which is covered or not covered by a non magnetic material including: generating a magnetic field that includes the magnetic material in a magnetic path, detecting a magnetic flux leakage with regard to the magnetic material by a GMR sensor, calculating a quantity of decrease in the thickness of a magnetic material based on an electrical signal output from the GMR sensor.

Effect of the Invention

According to the present invention, by using a GMR sensor having higher magnetic sensitivity than a magnetic sensor using a hall element, even if a magnetic material which is to be evaluated is covered by a non magnetic material, it is possible to precisely detect a leak magnetic flux. As a result, it is possible to precisely calculate a quantity of decrease in the thickness of a magnetic material such as a reinforcing steel or a steel plate or the like, it is possible to precisely perform quantitative evaluation of corrosion.

BEST MODE FOR CARRYING OUT THE INVENTION

Hereinbelow, an embodiment in accordance with the present invention shall be described with reference to the drawings.

Figure 1:
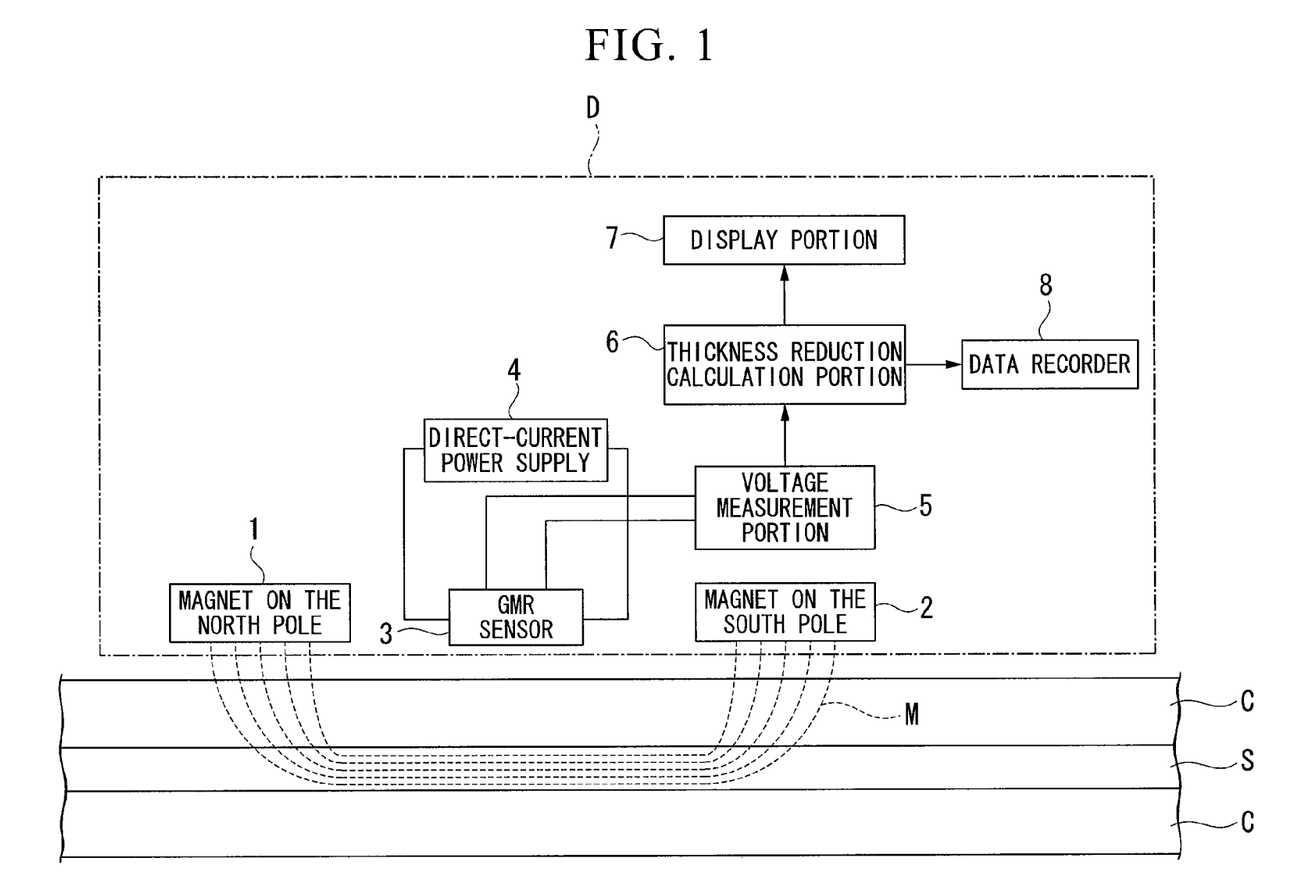
FIG. 1 is a constitutional block diagram showing a corrosion evaluation device D in accordance with an embodiment of the present invention.

FIG. 1 is a constitutional block diagram showing a corrosion evaluation device in accordance with the embodiment of the present invention. Here, the corrosion evaluation device D performs a quantitative evaluation of corrosion by measuring a quantity of decrease in the thickness of a reinforcing steel S (magnetic material) which is covered by concrete C (non magnetic material).

As shown in FIG. 1, the corrosion evaluation device D has a magnet 1 on the north pole, a magnet 2 on the south pole, a GMR (Giant Magnet-Resistive effect) sensor 3, a direct-current power supply 4, a voltage measurement portion 5, a thickness reduction calculation portion 6, a display portion 7, and a data recorder 8.

The magnet 1 on the north pole and the magnet 2 on the south pole (a magnetic field generating device) are permanent magnets, for example, and are respectively disposed on the concrete C in order to generate a magnetic field M which forms a magnetic path including a reinforcing steel S between both of the magnets.

Figure 2:
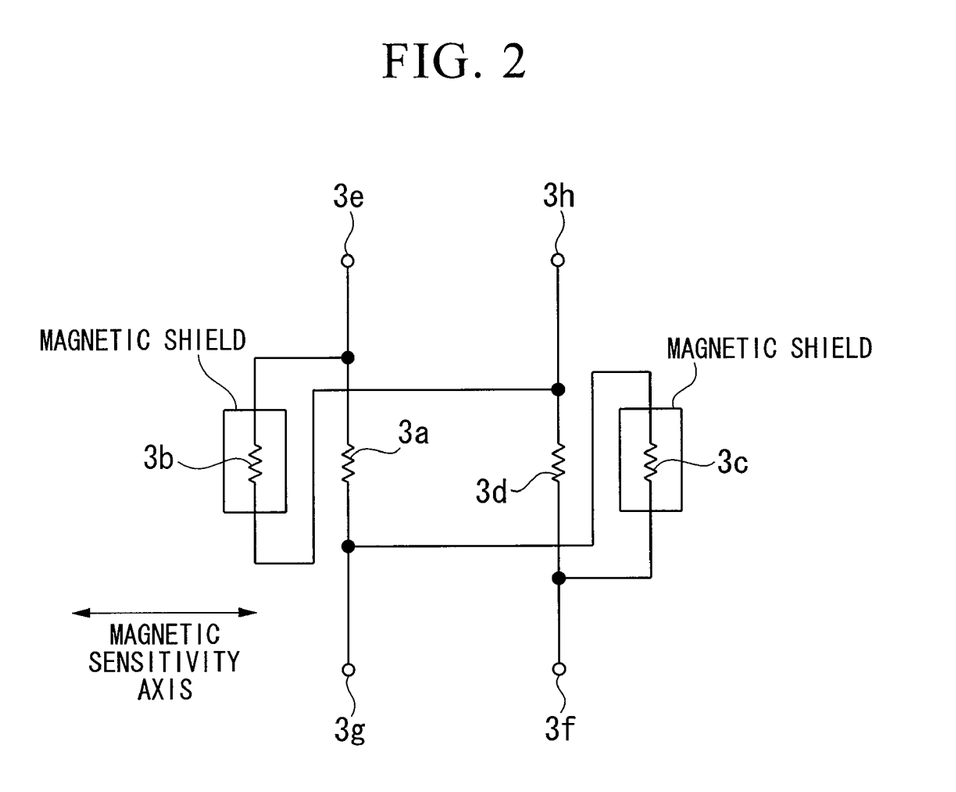
FIG. 2 is a circuit constitution diagram of a GMR sensor 3 in accordance with an embodiment of the present invention.

The GMR sensor 3 is comprised of a bridge circuit using a GMR element having a high magnetic sensitivity (that is, showing a great change in resistance relative to a change in magnetism) due to the Giant Magnet-Resistive effect. FIG. 2 shows an equivalent circuit for the GMR sensor 3. As shown in the figure, the GMR sensor 3 is comprised of a first GMR element 3a, a second GMR element 3b, a third GMR element 3c, a fourth GMR element 3d, a cathode power source terminal 3e, an anode power source terminal 3f, a first output terminal 3g, and a second output terminal 3h. Here, the GMR element can be described as a resistive element.

An end of the first GMR element 3a is connected to an end of the second GMR element 3b and a cathode power source terminal 3e while the other end of the first GMR element 3a is connected to an end of the third GMR element 3c and the first output terminal 3g. An end of the second GMR element 3b is connected to an end of the first GMR element 3a and a cathode power source terminal 3e while the other end of the second GMR element 3b is connected to an end of the fourth GMR element 3d and the second output terminal 3h. An end of the third GMR element 3c is connected to the other end of the first GMR element 3a and the first output terminal 3g while the other end of the third GMR element 3c is connected to the other end of the fourth GMR element 3d and the anode power source terminal 3f. An end of the fourth GMR element 3d is connected to the other end of the second GMR element 3b and the second output terminal 3h while the other end of the fourth GMR element 3d is connected to the other end of the third GMR element 3c and the anode power source terminal 3f.

The first GMR element 3a, the second GMR element 3b, the third GMR element 3c, and the fourth GMR element 3d have the same characteristics. Among these, a magnetic shield treatment is performed to the second GMR element 3b and the third GMR element 3c. Here, the cathode power source terminal 3e is connected to a cathode of the direct-current power supply 4 and the anode power source terminal 3f is connected to an anode of the direct-current power supply 4. The first output terminal 3g and the second output terminal 3h are connected to the voltage measurement portion 5.

Returning to FIG. 1, the GMR sensor 3 which is constituted like the circuit shown in FIG. 2 is disposed substantially in the central portion between the magnet 1 on the north pole and the magnet 2 on the south pole which are disposed apart. A magnetic sensitivity axis of the GMR sensor 3 is disposed so as to be perpendicular to the reinforcing steel S.

The direct-current power supply 4 is connected to the cathode power source terminal 3e and the anode power source terminal 3f of the GMR sensor 3 as described above and a direct-current voltage is supplied to the bridge circuit via these power source terminals. The voltage measurement portion 5 is connected to the first output terminal 3g and the second output terminal 3h of the GMR sensor 3 as described above, thereby allowing digital data (voltage data) showing the voltage value of the GMR sensor 3 to be output to the thickness reduction calculation portion 6. The thickness reduction calculation portion 6 calculates the quantity of decrease in the thickness of the reinforcing steel S based on the voltage data and outputs data showing the quantity of decrease in the thickness to the display portion 7, and the data recorder 8. The display portion 7 is a liquid crystal monitor, for example, for showing a measurement result of the quantity of decrease in the thickness based on the quantity of decrease in the thickness data. The data recorder 8 stores the quantity of decrease in the thickness data at each of the measurement points.

Next, the operation of the corrosion evaluation device D as constituted above shall be described.

Figure 3A:
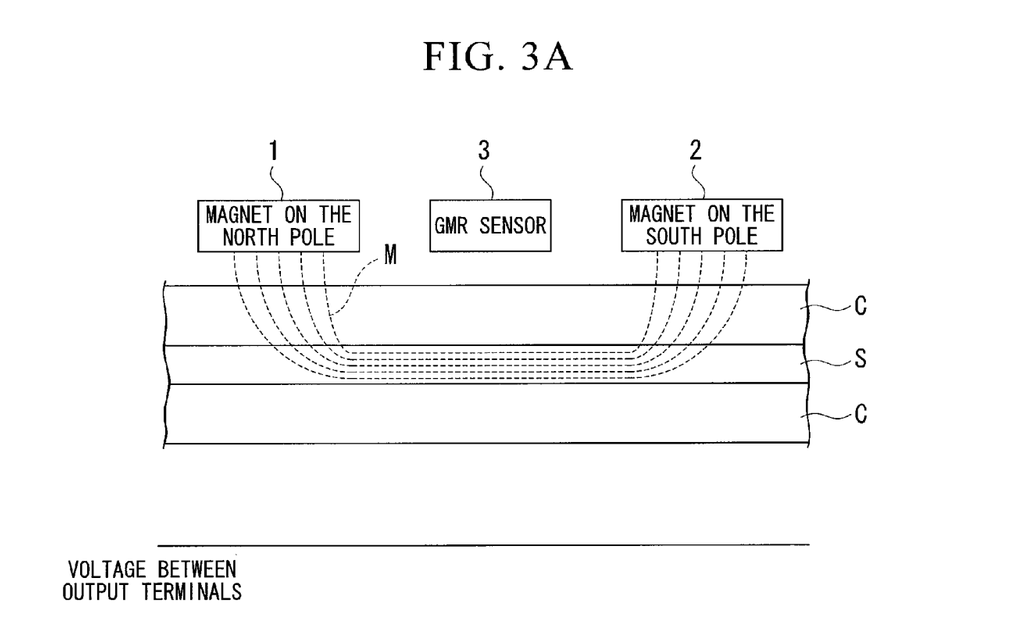
FIG. 3A is an explanatory diagram showing principle of a measurement of a quantity of decrease in the thickness in accordance with an embodiment of the present invention.

FIG. 3A shows a magnetic field M and a voltage between output terminals of the GMR sensor 3 when the thickness of the reinforcing steel S is not decreased, that is, corrosion is prevented in the reinforcing steel S. As shown in FIG. 3A, when the thickness of the reinforcing steel S is not decreased, the magnetic field M is uniformly formed along the reinforcing steel S, that is, the magnetic flux leakage is prevented.

In this case, in the bridge circuit of the GMR sensor 3 shown in FIG. 2, the first GMR element 3a, the second GMR element 3b, the third GMR element 3c, and the fourth GMR element 3d have the same resistance value. Accordingly, a voltage value between the first output terminal 3g and the second output terminal 3h, that is, a voltage between the output terminals of the GMR sensor 3 is zero. At this time, the thickness reduction calculation portion 6 calculates the quantity of decrease in the thickness as zero based on the voltage data showing the voltage between the output terminals as zero. The thickness reduction calculation portion 6 outputs the calculation result to the display portion 7 and the data recorder 8 as the quantity of decrease in the thickness data.

Figure 3B:
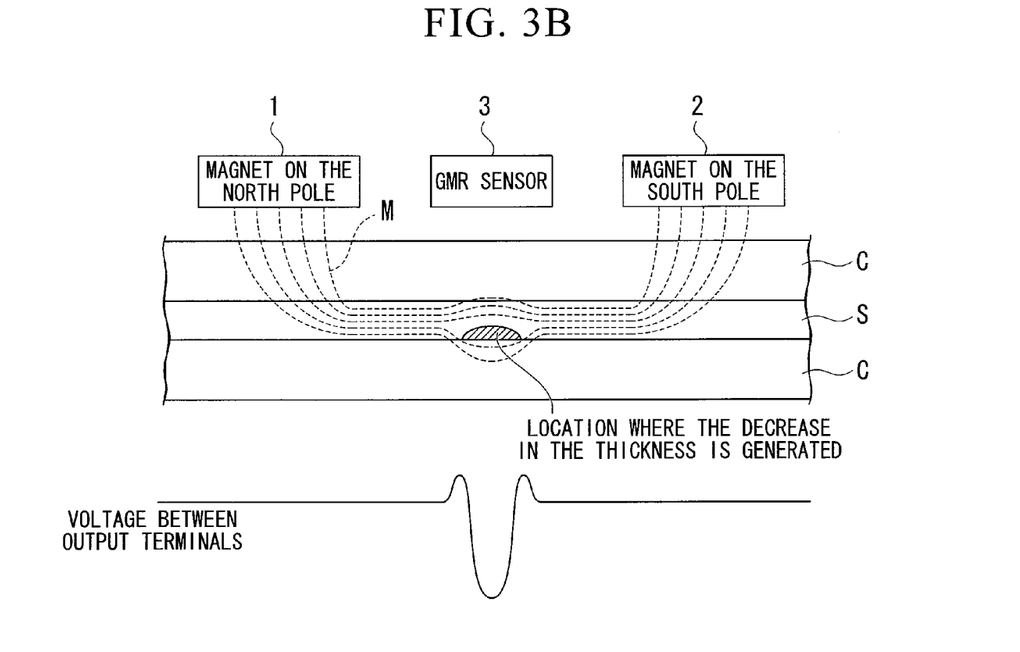
FIG. 3B is another other explanatory diagram showing principle of a measurement of a quantity of decrease in the thickness in accordance with an embodiment of the present invention.

FIG. 3B on the other hand shows the magnetic field M and the voltage between output terminals of the GMR sensor 3 when the thickness of the reinforcing steel S is decreased, that is, corrosion is generated in the reinforcing steel S. As shown in FIG. 3B, in a portion where the thickness of the reinforcing steel S is decreased, a change is generated in the magnetic field M, that is, a magnetic flux leakage is generated. The magnetic flux leakage changes to a greater extent as the quantity of decrease in the thickness becomes greater.

In this case, in the bridge circuit of the GMR sensor 3 shown in FIG. 2, the resistance values of the first GMR element 3a and the fourth GMR element 3d change in accordance with the change in the magnetic flux leakage while the resistance values of the second GMR element 3b and the third GMR element 3c do not change as they are performed with the magnetic shield treatment. Accordingly, an unbalance is generated in the bridge circuit; a voltage in accordance with the change in the magnetic flux leakage (that is, in proportional to the quantity of decrease in the thickness) is generated between the output terminals of the GMR sensor 3. That is, the following relationship (1) is valid between the voltage between the output terminals $V_0$ of the GMR sensor 3 and the quantity of decrease in the thickness $\Delta d$. Here, in the following relationship (1), k represents a proportionality factor.

$$\Delta d = k \cdot V_0 \tag{1}$$

Accordingly, the thickness reduction calculation portion 6 calculates the quantity of decrease in the thickness $\Delta d$ from the above relationship (1) and outputs the calculation result to the display portion 7 and the data recorder 8 as the quantity of decrease in the thickness data.

In the case of the reinforcing steel S being broken, a very large magnetic flux leakage is generated and the voltage between the output terminals $V_0$ of the GMR sensor 3 becomes a very large value. Therefore, a predetermined threshold value is set in advance, and when the voltage between the output terminals $V_0$ exceeding the threshold value is generated, the reinforcing steel S is determined to be broken and the result is displayed on the display portion 7 and stored in the data recorder 8.

Since the GMR sensor 3 has magnetic sensitivity which is 50 to 100 times higher than that of the hall element made of silicon, it is possible to precisely detect the magnetic flux leakage even if the reinforcing steel S is covered by the concrete C. As a result, the quantity of decrease in the thickness d which is calculated based on the voltage between the output terminals of the GMR sensor 3 is determined with high reliability. As described above, in accordance with the corrosion evaluation device D of the present embodiment, it is possible to precisely detect the magnetic flux leakage even if the reinforcing steel S, which is to be evaluated, is covered by a non magnetic material such as the concrete C or the like, and so it is possible to precisely perform a quantitative evaluation of corrosion.

Next, results of a corrosion evaluation experiment using the corrosion evaluation device D with regard to a composite floor slab, which is a complex formation of steel and concrete, shall be described.

Figure 4A:
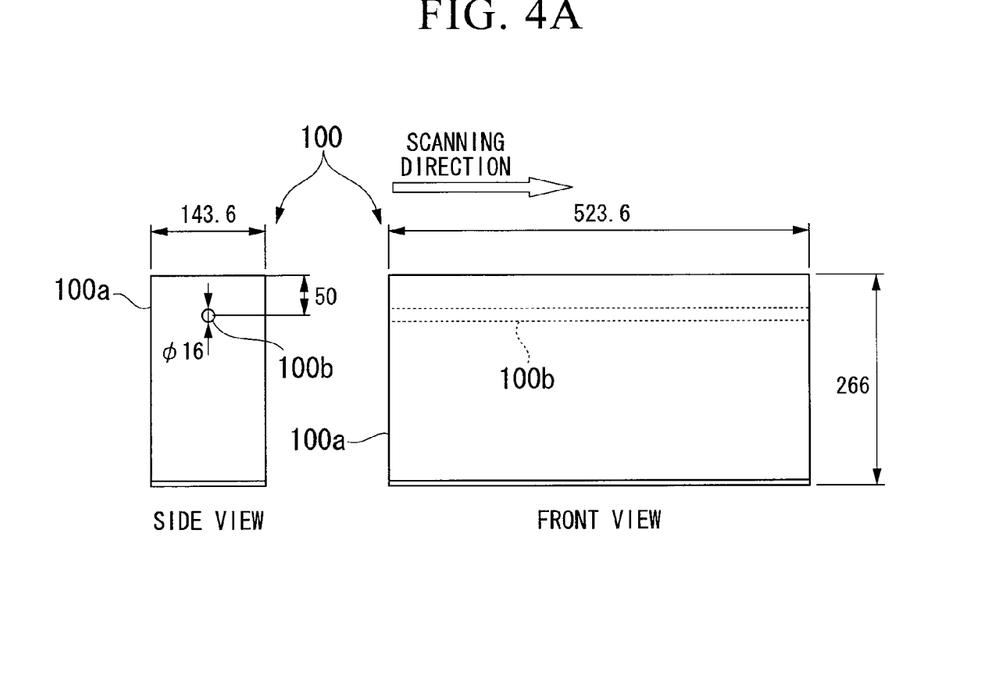
FIG. 4A is a first explanatory diagram of a corrosion evaluation experiment using the corrosion evaluation device D in accordance with an embodiment of the present invention.
Figure 4B:
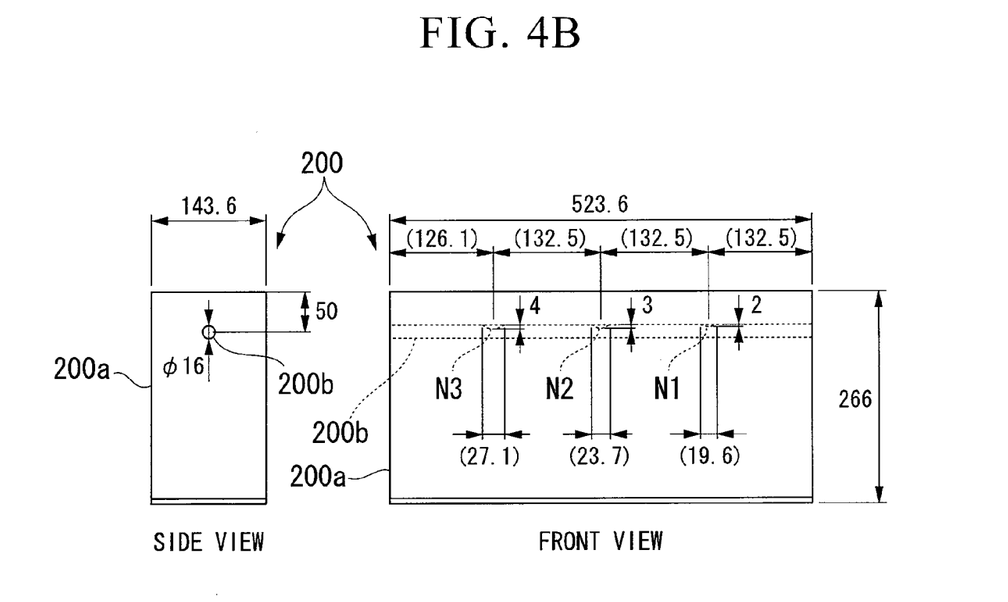
FIG. 4B is another first explanatory diagram of a corrosion evaluation experiment using the corrosion evaluation device D in accordance with an embodiment of the present invention.

FIG. 4A shows a side view and a front view of a test body 100 which is made of the composite floor slab used as a reference. This test body is a piece of concrete which is 266mm in height, 523.6mm in width, and 143.6mm in length and a deformed bar 100b with a diameter of 16mm is inserted therethrough. Here, the deformed bar 100b is inserted 50mm beneath the upper surface of the concrete piece 100a. On the other hand, FIG. 4B shows a side view and a front view of a test body 200 which is a complex formation of a deformed bar 200b and a concrete piece 200a added with notches N1 (2mm depth), N2 (3mm depth), and N3 (4mm depth) by a machining process in advance in order to simulate a decrease in the thickness due to corrosion.

The GMR sensor 3 of the corrosion evaluation device D is disposed on the upper surfaces of the test body 100 which is a reference and the test body 200 which simulates the decrease in the thickness. The GMR sensor 3 scans in the direction of the scanning direction shown in FIG. 4A and the voltage between the output terminals $V_0$ of the GMR sensor 3 at each of the locations of the sensor are measured.

Here, in order to facilitate the scanning, the scanning was performed with the GMR sensor 3 floated by 5 mm from the upper surface of each of the test bodies. An input voltage of the GMR sensor 3, that is a direct-current voltage supplied from the direct-current power supply 4, is set to 25V.

Figure 5:
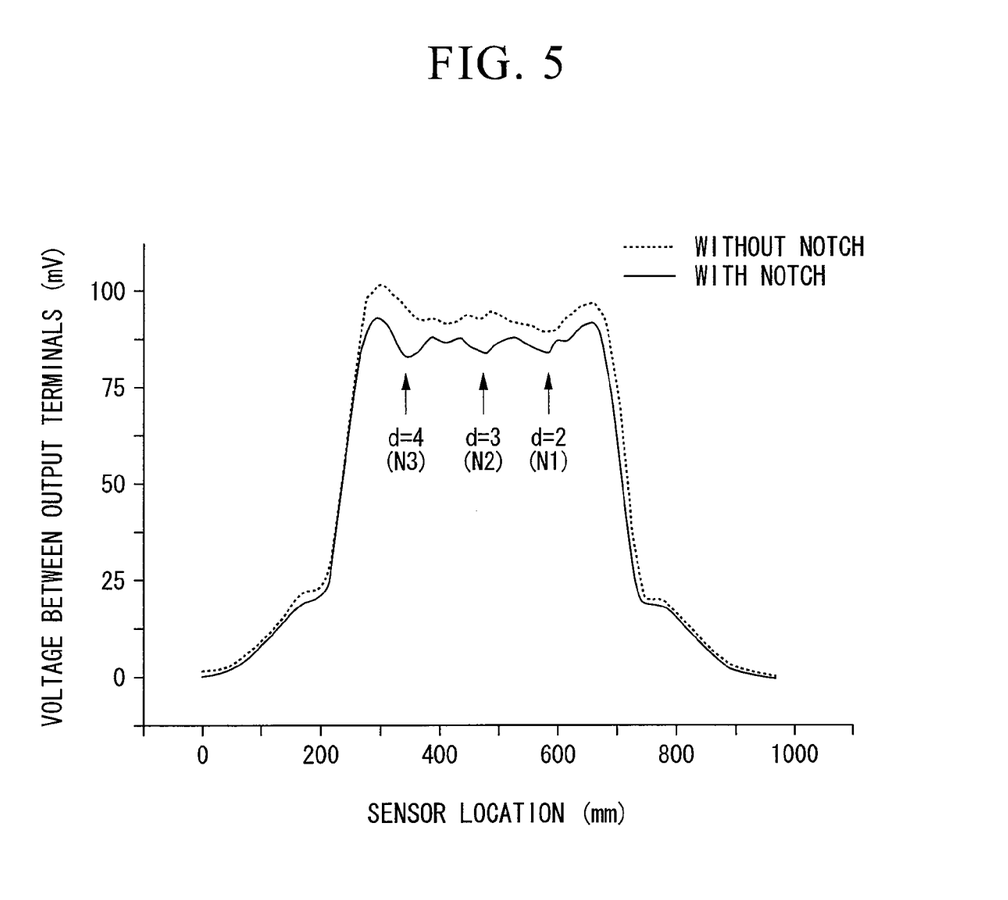
FIG. 5 is a second explanatory diagram of a corrosion evaluation experiment using the corrosion evaluation device D in accordance with an embodiment of the present invention.
Figure 6:
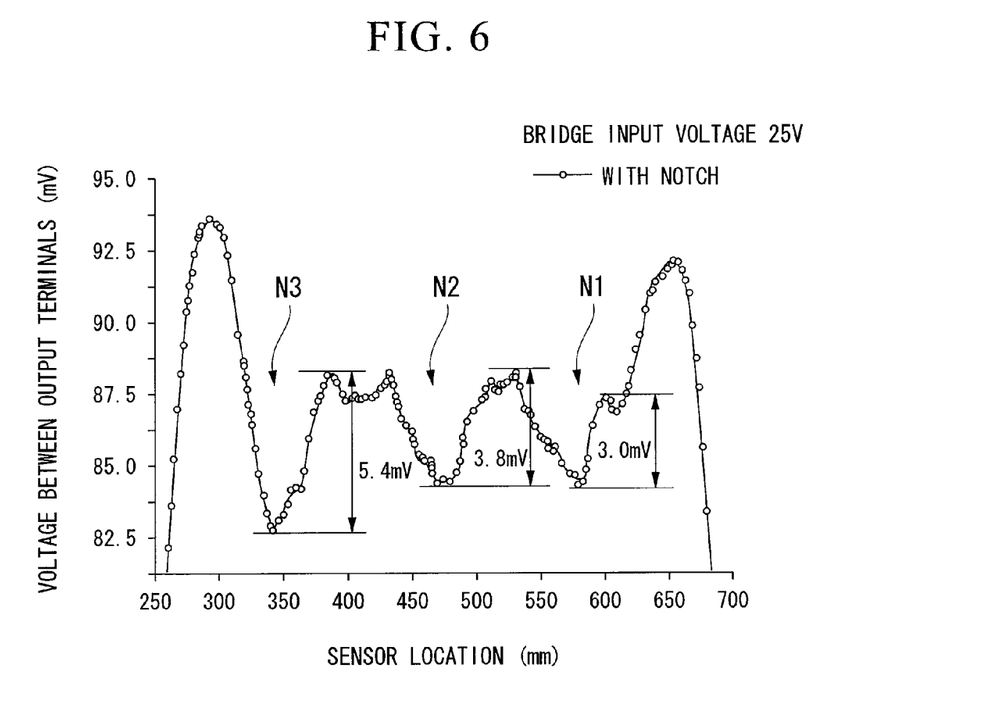
FIG. 6 is a third explanatory diagram of a corrosion evaluation experiment using the corrosion evaluation device D in accordance with an embodiment of the present invention.

FIG. 5 shows a voltage between the output terminals $V_0$-sensor position characteristics diagram. The horizontal axis shows the sensor position and the vertical axis shows the voltage between the output terminals $V_0$ of the GMR sensor 3. As shown in FIG. 5, by comparison to the test body 100 without notches as a reference, the test body 200 with notches N1 to N3 has fluctuations (valley portions) in the voltage between the output terminals $V_0$ at each position of the notches. FIG. 6 shows an enlarged view of the valley portions of the voltage between the output terminals $V_0$ at each position of the notches.

As shown in FIG. 6, it was found that a fluctuation which is 3.0 mV of signal width is generated in the voltage between the output terminals $V_0$ at the notch N1 (2 mm depth), a fluctuation which is 3.8 mV of signal width is generated in the voltage between the output terminals $V_0$ at the notch N2 (3 mm depth), and a fluctuation which is 5.4 mV of signal width is generated in the voltage between the output terminals $V_0$ at the notch N3 (4 mm depth).

Figure 7:
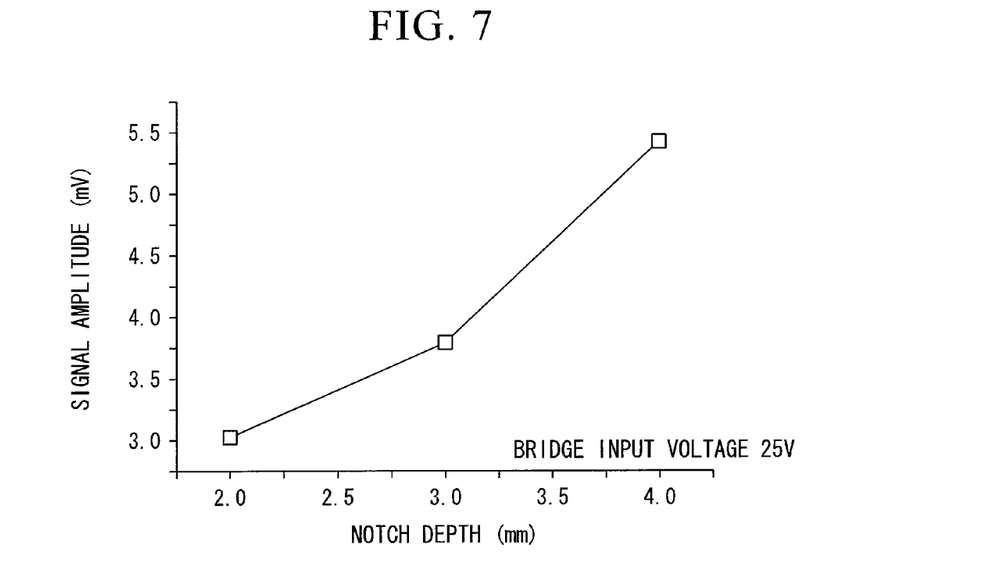
FIG. 7 is a fourth explanatory diagram of a corrosion evaluation experiment using the corrosion evaluation device D in accordance with an embodiment of the present invention.

FIG. 7 shows a correlation between the fluctuations of the voltage between the output terminals $V_0$ at each of the notch positions and the depth of the notches. In FIG. 7, the horizontal axis shows the notch depth and the vertical axis shows the fluctuations of the voltage between the output terminals $V_0$ (signal width). As shown in FIG. 7, it is confirmed that the notch depth, that is the quantity of decrease in the thickness d, and the fluctuations of the voltage between the output terminals $V_0$ of the GMR sensor 3 have a proportional relationship. That is, in accordance with this corrosion evaluation experiment, even if the magnetic material to be evaluated is covered by a non magnetic material, it is possible to perform an evaluation on corrosion quantitatively by using the corrosion evaluation device D.

Next, an application example of such a corrosion evaluation device D shall be described.

APPLICATION EXAMPLE 1

Figure 8:
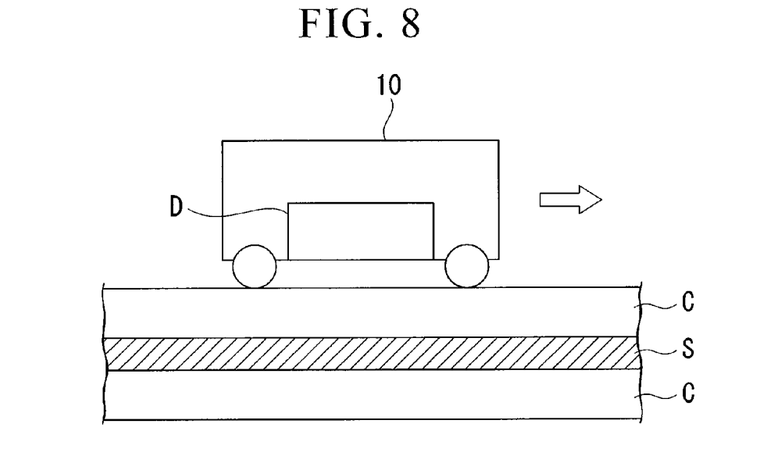
FIG. 8 is an application example 1 of the corrosion evaluation device D in accordance with an embodiment of the present invention.

FIG. 8 shows an application example of the corrosion evaluation device D. As shown in FIG. 8, the corrosion evaluation device D is disposed in the bogie 10 which is able to move itself by program control. The bogie 10 moves two-dimensionally along the concrete C which covers the reinforcing steel S and measures the quantity of decrease in the thickness at each of the predetermined measurement points. The quantity of decrease in the thickness measured at each of the measurement points is stored in the data recorder 8 one by one. In order to maintain the detection accuracy of the magnetic flux leakage, it is preferable to maintain a constant distance between the surface of the reinforcing steel S and the GMR sensor 3 (measurement gap). However, the surface of the concrete C is not always horizontal in accordance with measurement points on the surface of the concrete C. Accordingly, the bogie 10 has a function to compensate for the measurement gap at each of the measurement points in order to maintain the detection accuracy of the magnetic flux leakage.

In accordance with the application example 1 as described above, it is possible to effectively perform corrosion evaluation in a wide range in less time. Here, it is not limited to the bogie 10 which is provided with a program control, but it is possible to use a bogie which moves by wireless or wired operations.

APPLICATION EXAMPLE 2

Figure 9:
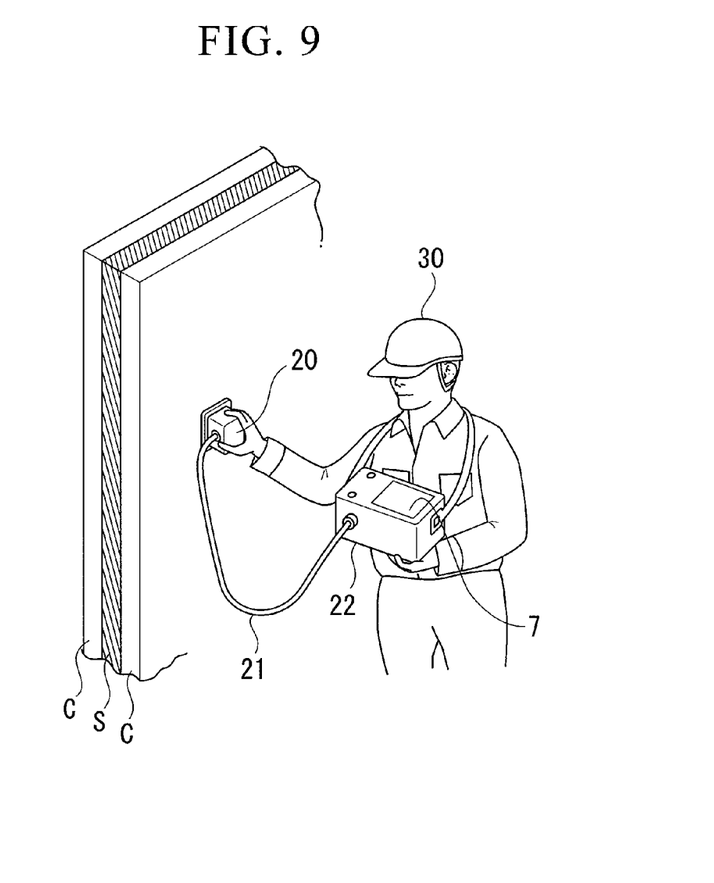
FIG. 9 is an application example 2 of the corrosion evaluation device D in accordance with an embodiment of the present invention.

FIG. 9 shows an application example 2 of the corrosion evaluation device D. As shown in FIG. 9, the corrosion evaluation device D of the application example 2 has a probe 20 provided with the magnet 1 on the north pole, the magnet 2 on the south pole, and the GMR sensor 3, and an operation box 22 connected via the probe 20 and a cable 21 provided with the direct-current power supply 4, a voltage measurement portion 5, the thickness reduction calculation portion 6, the display portion 7, and the data recorder 8. An operator 30 moves the probe 20 which is held in one hand to a preferred measurement point along the surface of the concrete C which covers the reinforcing steel S. At this time, the operator visually confirms the quantity of decrease in the thickness which is displayed on the display portion 7 of the operation box 22 and can recognize the progress of corrosion if any.

In accordance with the application example 2 as described above, it is possible to effectively perform corrosion evaluation for cases such as measuring the quantity of decrease in the thickness in such a narrow location that the bogie 10 of the application example 1 cannot pass through, measuring the quantity of decrease in the thickness of the reinforcing steel having a complicated three-dimensional structure, or when the number of measuring points are low.

The present invention is not limited to the above described embodiments but the following application examples can be considered.

(1) In the above described embodiments, the reinforcing steel covered by the concrete C is considered, however the present invention can also be applied to magnetic materials covered by other non magnetic materials. Performing corrosion evaluation on magnetic materials which are not covered by non magnetic materials is also possible.

(2) In the above described embodiments, GMR sensor 3 is comprised of a bridge circuit using a GMR element; however, other circuit structures are also available as long as they convert the change in the magnetic flux leakage to an electrical signal. A direct-current power supply is used for the power supply of the bridge circuit but an alternating-current power supply is also available.

INDUSTRIAL APPLICABILITY

In accordance with the corrosion evaluation device and the corrosion evaluation method, even when the magnetic material which is to be evaluated is covered by a non magnetic material, it is possible to precisely perform quantitative evaluation of corrosion.

What is claimed is:

1. A corrosion evaluation device for performing a quantitative evaluation of corrosion by measuring a quantity of decrease in the thickness of a magnetic material comprising:
    a magnetic field generating device for generating a magnetic field that includes the magnetic material in a magnetic path,
    a GMR sensor provided with a GMR element, which detects magnetic flux leakage with regard to the magnetic material, and converts a change in the magnetic flux into an electrical signal, and
    a thickness reduction calculation portion for calculating a quantity of decrease in the thickness of the magnetic material based on the electrical signal, wherein
    the magnetic field generating device includes a first magnet and a second magnet which are arranged along a side of the magnetic material, and the GMR sensor is disposed between the first and second magnets.

2. The corrosion evaluation device in accordance with claim 1, wherein
    the GMR sensor is comprised of a bridge circuit using the GMR element.

3. The corrosion evaluation device in accordance with claim 1, wherein
    the device measures the quantity of decrease in the thickness at each of predetermined measuring points by two-dimensionally moving along the magnetic material.

4. The corrosion evaluation device in accordance with claim 3, wherein
    the device moves while maintaining a constant distance between a surface of the magnetic material and the GMR sensor.

5. The corrosion evaluation device in accordance with claim 1,
    wherein the magnetic material is a reinforcing steel or a steel plate.

6. The corrosion evaluation device in accordance with claim 1,
    wherein the magnetic material is covered with a non-magnetic material and the non magnetic material is concrete.

7. A corrosion evaluation method for performing a quantitative evaluation of corrosion by measuring a quantity of decrease in the thickness of a magnetic material comprising the steps of:
    generating a magnetic field, that includes the magnetic material in a magnetic path, by a first magnet and a second magnet, the first magnet and the second magnet being arranged along a side of the magnetic material,
    detecting a magnetic flux leakage with regard to the magnetic material by a GMR sensor disposed between the first and second magnets, and
    calculating a quantity of decrease in the thickness of a magnetic material based on an electrical signal output from the GMR sensor.

8. The corrosion evaluation device in accordance with claim 1,
    wherein the GMR sensor is disposed in a central region between the first and second magnets.

9. The corrosion evaluation method in accordance with claim 7, further comprising the step of disposing the GMR sensor in a central region between the first and second magnets.

* * * * *